(12) United States Patent
Szperka et al.

(10) Patent No.: US 11,604,680 B2
(45) Date of Patent: Mar. 14, 2023

(54) LOW SYSTEM MEMORY DETECTION

(71) Applicant: ARRIS Enterprises LLC, Suwanee, GA (US)

(72) Inventors: Douglas R. Szperka, Oreland, PA (US); Ernest G. Schmitt, Maple Glen, PA (US); Rathnakar Shetty, Doylestown, PA (US); Sandeep Guddekoppa Suresh, Bangalore (IN)

(73) Assignee: ARRIS Enterprises LLC, Suwanee, GA (US)

( * ) Notice: Subject to any disclaimer, the term of this patent is extended or adjusted under 35 U.S.C. 154(b) by 116 days.

(21) Appl. No.: 16/126,460

(22) Filed: Sep. 10, 2018

(65) Prior Publication Data

US 2019/0087230 A1 Mar. 21, 2019

Related U.S. Application Data

(60) Provisional application No. 62/555,903, filed on Sep. 8, 2017.

(51) Int. Cl.
| | |
|---|---|
| *G06F 9/44* | (2018.01) |
| *G06F 9/50* | (2006.01) |
| *B01J 31/24* | (2006.01) |
| *C07C 2/86* | (2006.01) |
| *C07C 67/343* | (2006.01) |
| *C07D 213/30* | (2006.01) |
| *C07D 215/06* | (2006.01) |

(Continued)

(52) U.S. Cl.
CPC ........ *G06F 9/5022* (2013.01); *B01J 31/2452* (2013.01); *C07C 2/868* (2013.01); *C07C 67/343* (2013.01); *C07D 213/30* (2013.01); *C07D 215/06* (2013.01); *C07D 493/10* (2013.01); *C07F 9/6561* (2013.01); *C07F 15/0033* (2013.01); *G06F 9/485* (2013.01); *G06F 9/5016* (2013.01); *G06F 11/3037* (2013.01); *B01J 2231/32* (2013.01); *B01J 2231/4261* (2013.01); *B01J 2231/44* (2013.01); *B01J 2231/646* (2013.01); *B01J 2531/824* (2013.01); *B01J 2531/827* (2013.01); *C07C 2603/86* (2017.05); *G06F 2201/81* (2013.01)

(58) Field of Classification Search
CPC ..................................................... G06F 9/5022
USPC .......................................................... 718/104
See application file for complete search history.

(56) References Cited

U.S. PATENT DOCUMENTS

2012/0324481 A1* 12/2012 Xia .......................... G06F 9/485
719/320
2017/0371561 A1* 12/2017 Cai ........................... G06F 13/16

* cited by examiner

*Primary Examiner* — Timothy A Mudrick
(74) *Attorney, Agent, or Firm* — Panitch Schwarze Belisario & Nadel LLC

(57) ABSTRACT

Methods, systems, and computer readable media may be operable to facilitate an anticipation of an execution of a process termination tool. An allocation stall counter may be queried at a certain frequency, and from the query of the allocation stall counter, a number of allocation stall counter increments occurring over a certain duration of time may be determined. If the number of allocation stall counter increments is greater than a threshold, a determination may be made that system memory is running low and that an execution of a process termination tool is imminent. In response to the determination that system memory is running low, a flag indicating that system memory is running low may be set, and one or more programs, in response to reading the flag, may free memory that is not necessary or required for execution.

14 Claims, 4 Drawing Sheets

(51) Int. Cl.
*C07D 493/10* (2006.01)
*C07F 9/6561* (2006.01)
*C07F 15/00* (2006.01)
*G06F 9/48* (2006.01)
*G06F 11/30* (2006.01)

LOW SYSTEM MEMORY DETECTION

CROSS REFERENCE TO RELATED APPLICATION

This application is a non-provisional application claiming the benefit of U.S. Provisional Application Ser. No. 62/555,903, entitled "Low System Memory Detection," which was filed on Sep. 8, 2017, and is incorporated herein by reference in its entirety.

TECHNICAL FIELD

This disclosure relates to the detection of low system memory.

BACKGROUND

Typically, when a Linux-based system runs low on an amount of memory available, an operating system executes a process termination tool (e.g., OOM (out-of-memory) killer), that terminates one or more process(es) according to certain heuristics in order to free up memory for further allocations. However, multi-process systems running on Linux can be adversely affected when a core process is terminated by the process termination tool. Anticipation of an execution of a process termination tool is impeded by an ability to overcommit available memory. Therefore, a need exists for improved methods and systems for avoiding the adverse effects of a process termination tool execution.

BRIEF DESCRIPTION OF THE DRAWINGS

Like reference numbers and designations in the various drawings indicate like elements.

DETAILED DESCRIPTION

It is desirable to provide methods and systems operable to anticipate an execution of a process termination tool. Methods, systems, and computer readable media may be operable to facilitate an anticipation of an execution of a process termination tool. An allocation stall counter may be queried at a certain frequency, and from the query of the allocation stall counter, a number of allocation stall counter increments occurring over a certain duration of time may be determined. If the number of allocation stall counter increments is greater than a threshold, a determination may be made that system memory is running low and that an execution of a process termination tool is imminent. In response to the determination that system memory is running low, a flag indicating that system memory is running low may be set, and one or more programs, in response to reading the flag, may free memory that is not necessary or required for execution.

Figure 1:
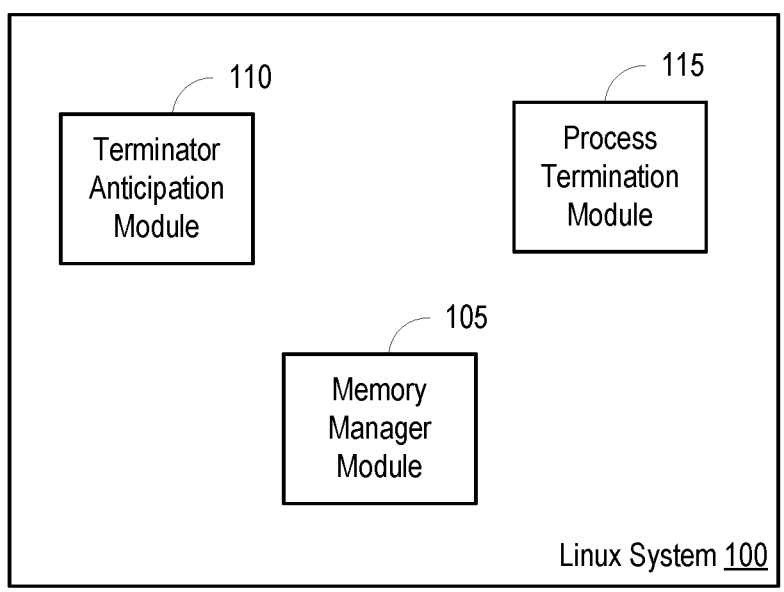
FIG. 1 is a block diagram illustrating an example Linux system operable to facilitate an anticipation of an execution of a process termination tool.

FIG. 1 is a block diagram illustrating an example Linux system 100 operable to facilitate an anticipation of an execution of a process termination tool. The Linux system 100 may include a memory manager module 105, a terminator anticipation module 110, and a process termination module 115. The memory manager module 105 may be a Linux virtual memory management system.

In embodiments, the memory manager module 105 may initiate an execution of the process termination module 115 in response to a determination that more memory is needed for allocation. For example, the memory manager module 105 may make the determination that there is not enough memory available for allocation to accommodate an application or process. In response to the determination that there is not enough memory available for allocation, the memory manager module 105 may cause the process termination module 115 to terminate one or more application or processes in order to free up some memory. The process termination module 115 may be a process termination tool (e.g., OOM killer). When executed, the process termination module 115 may select and terminate one or more ongoing applications or processes.

In embodiments, the terminator anticipation module 110 may anticipate an execution of the process termination module 115. The terminator anticipation module 110 may monitor a count of memory allocation stalls. For example, the terminator anticipation module 110 may query an allocation stall (e.g., allocstall) counter that is exposed by the memory manager module 105. The allocation stall counter may be queried from a vmstat file under a /proc filesystem. During system execution, a timer may be set to query the value for the allocstall counter in /proc/vmstat with a specific frequency, and the terminator anticipation module 110 may query the allocation stall counter at each expiration of the timer.

In embodiments, the terminator anticipation module 110 may determine whether a number of increments of the allocation stall counter exceeds a threshold over a certain duration. When the terminator anticipation module 110 determines that more than a threshold number of allocation stall counter increments have occurred over the certain duration, the terminator anticipation module 110 may determine that the memory manager module 105 is experiencing difficulties in obtaining a free page and the terminator anticipation module 110 may anticipate an execution of the process termination module 115. When the terminator anticipation module 110 determines that more than a threshold number of allocation stall counter increments have occurred over the certain duration, the terminator anticipation module 110 may determine that the Linux system 100 is low on available memory and may set a flag that may be read by each of one or more programs of the Linux system 100, wherein the flag provides an indication that the Linux system 100 is low on available memory. For example, if the value of the allocation stall counter increases by a certain amount within one query of /proc/vmstat, a flag, readable by all user-space programs, may be set to indicate that the system is low on memory.

In embodiments, when the flag indicating low system memory is set, the terminator anticipation module 110 may monitor a free memory statistic (e.g., a free memory indicator such as a MemFree statistic in a meminfo file of a /proc filesystem) that is maintained at the memory manager module 105, and when enough memory is freed, as determined by a spike in the free memory statistic, the terminator anticipation module 110 may clear the flag indicating low system memory. With the flag being readable by one or more programs, the programs, in response to reading the flag, may free memory that is not necessary or required for execution (e.g., caches and other discardable types of memory), and the value of MemFree in /proc/meminfo may be monitored for a spike in free memory that results when such programs take action (e.g., when one or more programs free memory that is not required or necessary). The system low memory flag may then be cleared if the value for MemFree in /proc/meminfo increases beyond a certain amount within a specified timeframe, and the current value of the allocation stall counter in /proc/vmstat may be saved or recorded for the next test of low system memory (i.e., to account for a scenario in which the value of the counter spikes in response to a large block of memory being suddenly freed).

Figure 2:
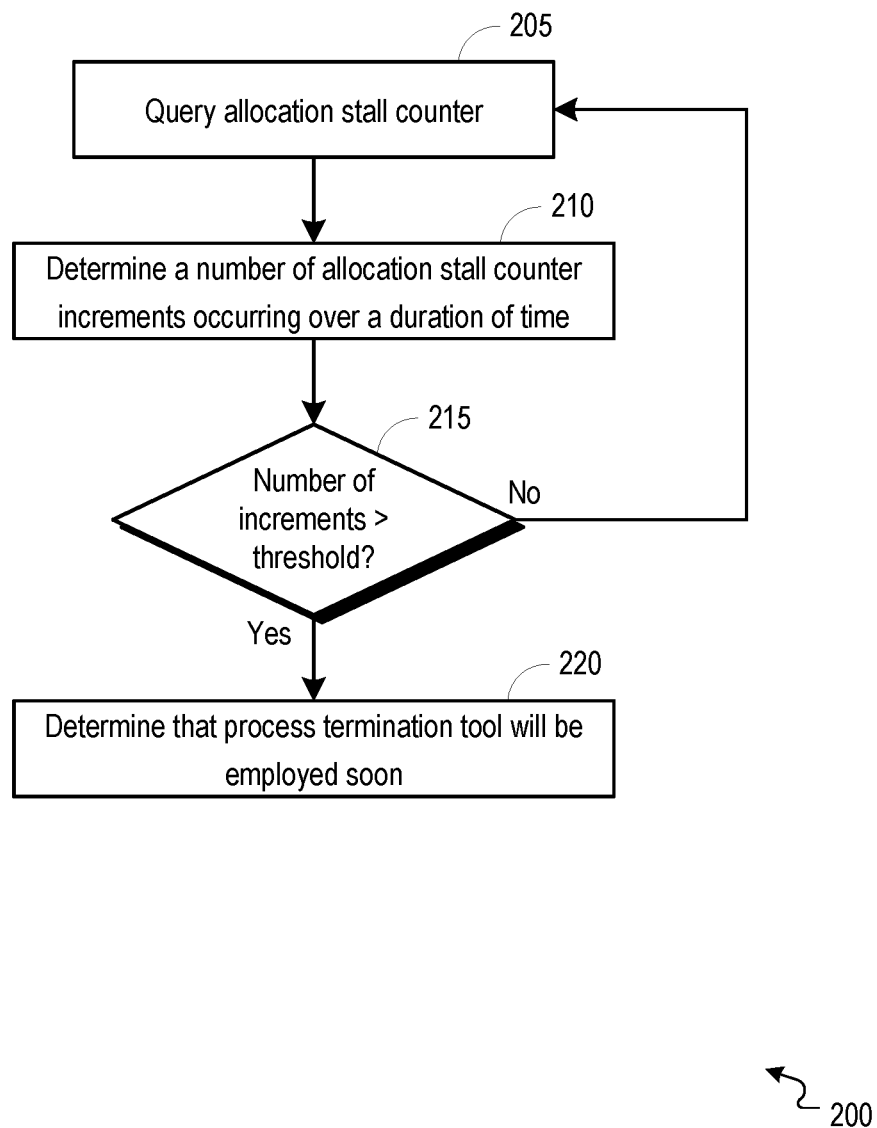
FIG. 2 is a flowchart illustrating an example process operable to anticipate an execution of a process termination tool.

FIG. 2 is a flowchart illustrating an example process 200 operable to anticipate an execution of a process termination tool. The process 200 may start at 205, where an allocation stall counter is queried. The allocation stall counter may be queried, for example, by a terminator anticipation module 110 of FIG. 1. In embodiments, the terminator anticipation module 110 may query an allocation stall (e.g., allocstall) counter that is exposed by a memory management system (e.g., a memory manager module 105 of FIG. 1). The terminator anticipation module 110 may query the allocation stall counter at a specific frequency.

At 210, a number of allocation stall counter increments occurring over a certain duration of time may be determined. The number of allocation stall counter increments occurring over a certain duration of time may be determined, for example, by the terminator anticipation module 110. In embodiments, the terminator anticipation module 110 may compare queried allocation stall counter values to determine a number of increments to the allocation stall counter that have occurred over a certain duration of time.

At 215, a determination may be made whether the number of allocation stall counter increments is greater than a threshold. The determination whether the number of allocation stall counter increments is greater than a threshold may be made, for example, by the terminator anticipation module 110. In embodiments, the terminator anticipation module 110 may compare the number of allocation stall counter increments (e.g., the number of increments determined at 210) to a threshold number of allocation stall counter increments. If the determination is made that the number of allocation stall counter increments is not greater than the threshold, the allocation stall counter may be queried at 205. The allocation stall counter may be queried at 205 following a delay of a certain duration (e.g., the duration being equivalent to a certain frequency at which the allocation stall counter is to be determined).

If, at 215, the determination is made that the number of allocation stall counter increments is greater than the threshold, the process 200 may proceed to 220. At 220, a determination may be made that a process termination tool will be employed soon. The determination that a process termination tool will be employed soon may be made, for example, by the terminator anticipation module 110. In embodiments, the terminator anticipation module 110 may determine that an initiation of a process termination tool (e.g., process termination module 115 of FIG. 1) is imminent.

Figure 3:
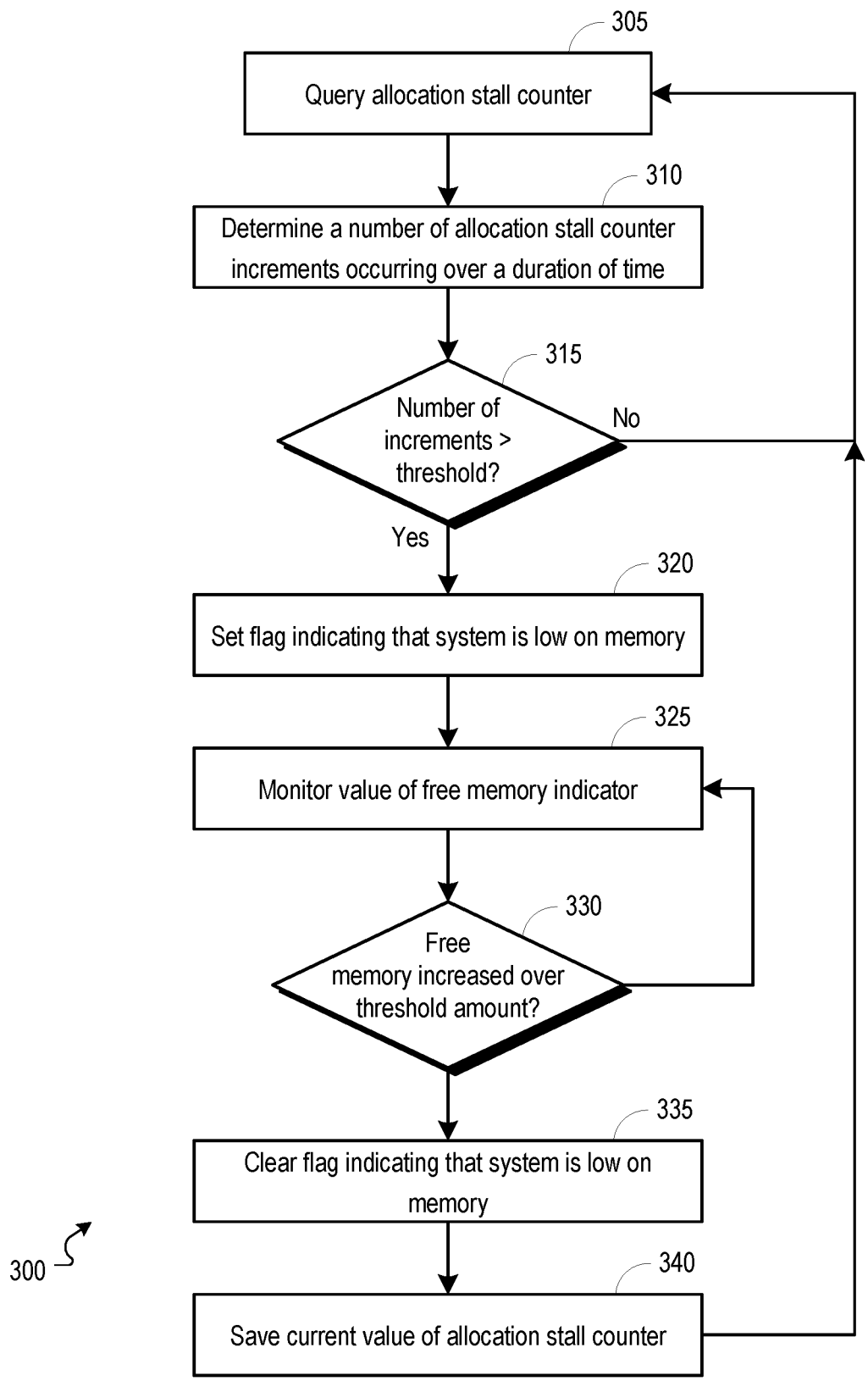
FIG. 3 is a flowchart illustrating an example process operable to respond to a detection of low memory.

FIG. 3 is a flowchart illustrating an example process 300 operable to respond to a detection of low memory. The process 300 may start at 305, where an allocation stall counter is queried. The allocation stall counter may be queried, for example, by a terminator anticipation module 110 of FIG. 1. In embodiments, the terminator anticipation module 110 may query an allocation stall (e.g., allocstall) counter that is exposed by a memory management system (e.g., a memory manager module 105 of FIG. 1). The terminator anticipation module 110 may query the allocation stall counter at a specific frequency.

At 310, a number of allocation stall counter increments occurring over a certain duration of time may be determined. The number of allocation stall counter increments occurring over a certain duration of time may be determined, for example, by the terminator anticipation module 110. In embodiments, the terminator anticipation module 110 may compare queried allocation stall counter values to determine a number of increments to the allocation stall counter that have occurred over a certain duration of time.

At 315, a determination may be made whether the number of allocation stall counter increments is greater than a threshold. The determination whether the number of allocation stall counter increments is greater than a threshold may be made, for example, by the terminator anticipation module 110. In embodiments, the terminator anticipation module 110 may compare the number of allocation stall counter increments (e.g., the number of increments determined at 310) to a threshold number of allocation stall counter increments. If the determination is made that the number of allocation stall counter increments is not greater than the threshold, the allocation stall counter may be queried at 305. The allocation stall counter may be queried at 305 following a delay of a certain duration (e.g., the duration being equivalent to a certain frequency at which the allocation stall counter is to be determined).

If, at 315, the determination is made that the number of allocation stall counter increments is greater than the threshold, the process 300 may proceed to 320. At 320, a flag indicating low system memory may be set. The flag indicating low system memory may be set, for example, by the terminator anticipation module 110. In embodiments, the flag may be readable by one or more programs or applications associated with the system (e.g., Linux system 100 of FIG. 1). In response to a reading or detection of the flag, one or more programs or applications may take action to free memory that is not necessary or required for the programs or applications to effectively execute, and these actions may result in a spike in free memory that may be identified from the free memory indicator.

In embodiments, when the flag indicating that the system is low on memory is set, a value of a free memory indicator may be monitored at 325. For example, the terminator anticipation module 110 may monitor free memory statistics that are maintained at the memory manager module 105 of FIG. 1.

At 330, a determination may be made whether free memory has increased over a threshold amount. In embodiments, the terminator anticipation module 110 may determine whether a monitored free memory indicator increases above a threshold amount. If the determination is made that free memory of the system (e.g., Linux system 100 of FIG. 1) as indicated by the free memory indicator exceeds the threshold amount, the flag indicating that system memory is low may be cleared 335, and the current value of the allocation stall counter may be saved at 340. If the determination is made that free memory of the system as indicated by the free memory indicator does not exceed the threshold amount, the flag indicating that system memory is low may be maintained and the value of the free memory indicator may continue to be monitored 325.

Figure 4:
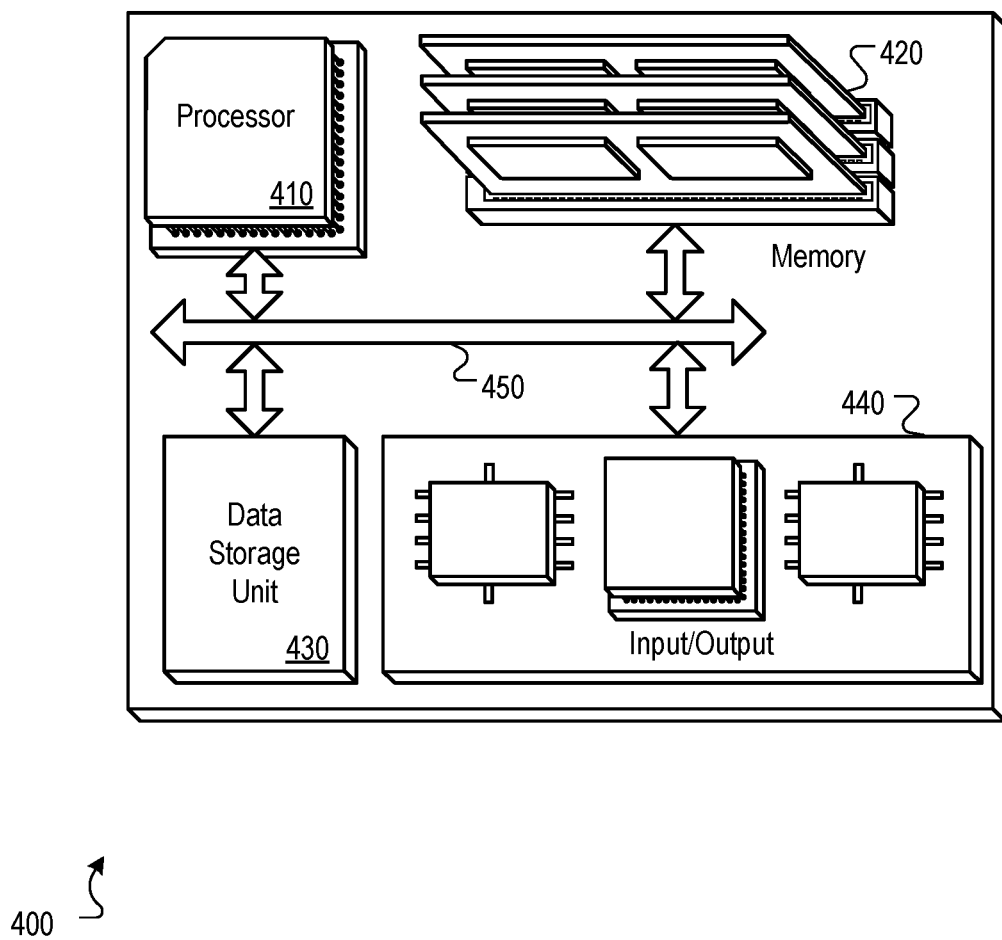
FIG. 4 is a block diagram of a hardware configuration operable to facilitate an anticipation of an execution of a process termination tool.

FIG. 4 is a block diagram of a hardware configuration 400 operable to facilitate an anticipation of an execution of a process termination tool. The hardware configuration 400 can include a processor 410, a memory 420, a storage device 430, and an input/output device 440. Each of the components 410, 420, 430, and 440 can, for example, be interconnected using a system bus 450. The processor 410 can be capable of processing instructions for execution within the hardware configuration 400. In one implementation, the processor 410 can be a single-threaded processor. In another implementation, the processor 410 can be a multi-threaded processor. The processor 410 can be capable of processing instructions stored in the memory 420 or on the storage device 430. It should be understood that the hardware configuration 400 may further include a transcoder configured to support format conversion of content.

The memory 420 can store information within the hardware configuration 400. In one implementation, the memory 420 can be a computer-readable medium. In one implementation, the memory 420 can be a volatile memory unit. In another implementation, the memory 420 can be a non-volatile memory unit.

In some implementations, the storage device 430 can be capable of providing mass storage for the hardware configuration 400. In one implementation, the storage device 430 can be a computer-readable medium. In various different implementations, the storage device 430 can, for example, include a hard disk device, an optical disk device, flash memory or some other large capacity storage device. In other implementations, the storage device 430 can be a device external to the hardware configuration 400.

The input/output device 440 provides input/output operations for the hardware configuration 400. In one implementation, the input/output device 440 can include one or more of a network interface device (e.g., an Ethernet card), a serial communication device (e.g., an RS-232 port), one or more universal serial bus (USB) interfaces (e.g., a USB 2.0 port), one or more wireless interface devices (e.g., an 802.11 card), and/or one or more interfaces for outputting video and/or data services to a multimedia device (e.g., access point, gateway device, STB (set-top box), content storage device, cable modem, router, wireless extender, or other access device) or client device (e.g., STB, computer, television, tablet, mobile device, etc.). In another implementation, the input/output device can include driver devices configured to send communications to, and receive communications from one or more networks (e.g., WAN (wide-area network), local network, provider network, etc.).

Those skilled in the art will appreciate that the invention described herein improves upon methods and systems for anticipating an execution of a process termination tool. Methods, systems, and computer readable media may be operable to facilitate an anticipation of an execution of a process termination tool. An allocation stall counter may be queried at a certain frequency, and from the query of the allocation stall counter, a number of allocation stall counter increments occurring over a certain duration of time may be determined. If the number of allocation stall counter increments is greater than a threshold, a determination may be made that system memory is running low and that an execution of a process termination tool is imminent. In response to the determination that system memory is running low, a flag indicating that system memory is running low may be set, and one or more programs, in response to reading the flag, may free memory that is not necessary or required for execution.

The subject matter of this disclosure, and components thereof, can be realized by instructions that upon execution cause one or more processing devices to carry out the processes and functions described above. Such instructions can, for example, comprise interpreted instructions, such as script instructions, e.g., JavaScript or ECMAScript instructions, or executable code, or other instructions stored in a computer readable medium.

Implementations of the subject matter and the functional operations described in this specification can be provided in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus.

A computer program (also known as a program, software, software application, script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification are performed by one or more programmable processors executing one or more computer programs to perform functions by operating on input data and generating output thereby tying the process to a particular machine (e.g., a machine programmed to perform the processes described herein). The processes and logic flows can also be performed by, and apparatus can also be implemented as, special purpose logic circuitry, e.g., an FPGA (field programmable gate array) or an ASIC (application specific integrated circuit).

Computer readable media suitable for storing computer program instructions and data include all forms of non-volatile memory, media and memory devices, including by way of example semiconductor memory devices (e.g., EPROM, EEPROM, and flash memory devices); magnetic disks (e.g., internal hard disks or removable disks); magneto optical disks; and CD ROM and DVD ROM disks. The processor and the memory can be supplemented by, or incorporated in, special purpose logic circuitry.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter described in this specification have been described. Other embodiments are within the scope of the following claims. For example, the actions recited in the claims can be performed in a different order and still achieve desirable results, unless expressly noted otherwise. As one example, the processes depicted in the accompanying figures do not necessarily require the particular order shown, or sequential order, to achieve desirable results. In some implementations, multitasking and parallel processing may be advantageous.

We claim:

1. A method comprising:
   querying an allocation stall counter;
   based on the query of the allocation stall counter, determining a number of allocation stall counter increments occurring over a certain duration of time;
   in response to the number of allocation stall counter increments occurring over the certain duration of time is greater than a threshold, determining that an execution of a process termination tool is imminent; and
   in response to the determination that an execution of a process termination tool is imminent, setting a flag indicating that a system associated with the allocation stall counter is low on available memory, wherein the flag is readable by one or more processes that are running on the system, wherein one or more of the processes respond by freeing at least a portion of memory used by the one or more processes.

2. The method of claim 1, further comprising:
   monitoring a free memory indicator; and
   determining free memory available to the system increases over a threshold amount; and
   in response to determining free memory available to the system increases of the threshold amount, clearing the flag.

3. The method of claim 2, further comprising:
   saving the value of the allocation stall counter for use in a subsequent low memory test.

4. The method of claim 1, wherein the allocation stall counter is associated with a Linux system.

5. The method of claim 1, wherein the allocation stall counter is queried at a predetermined frequency.

6. An apparatus comprising one or more modules that:
   query an allocation stall counter;
   based on the query of the allocation stall counter, determine a number of allocation stall counter increments occurring over a certain duration of time;
   in response to the number of allocation stall counter increments occurring over the certain duration of time is greater than a threshold, determines that an execution of a process termination tool is imminent; and
   in response to the determination that an execution of a process termination tool is imminent, set a flag indicating that a system associated with the allocation stall counter is low on available memory, wherein the flag is readable by one or more processes that are running on the system, wherein one or more of the processes respond by freeing at least a portion of memory used by the one or more processes.

7. The apparatus of claim 6, wherein the one or more modules further:
   monitor a free memory indicator; and
   determining free memory available to the system increases over a threshold amount; and
   in response to determining free memory available to the system increases of the threshold amount, clear the flag.

8. The apparatus of claim 7, wherein the one or more modules further:
   save the value of the allocation stall counter for use in a subsequent low memory test.

9. The apparatus of claim 6, wherein the allocation stall counter is queried at a predetermined frequency.

10. One or more non-transitory computer readable media having instructions operable to cause one or more processors to perform the operations comprising:
    querying an allocation stall counter;
    based on the query of the allocation stall counter, determining a number of allocation stall counter increments occurring over a certain duration of time;
    in response to the number of allocation stall counter increments occurring over the certain duration of time is greater than a threshold, determining that an execution of a process termination tool is imminent; and
    in response to the determination that an execution of a process termination tool is imminent, setting a flag indicating that a system associated with the allocation stall counter is low on available memory, wherein the flag is readable by one or more processes that are running on the system, wherein one or more of the processes respond by freeing at least a portion of memory used by the one or more processes.

11. The one or more non-transitory computer-readable media of claim 10, wherein the instructions are further operable to cause the one or more processors to perform the operations comprising:
    monitoring a free memory indicator; and
    determining free memory available to the system increases over a threshold amount; and
    in response to determining free memory available to the system increases of the threshold amount, clearing the flag.

12. The one or more non-transitory computer-readable media of claim 11, wherein the instructions are further operable to cause the one or more processors to perform the operations comprising:
    saving the value of the allocation stall counter for use in a subsequent low memory test.

13. The one or more non-transitory computer-readable media of claim 10, wherein the allocation stall counter is associated with a Linux system.

14. The one or more non-transitory computer-readable media of claim 10, wherein the allocation stall counter is queried at a predetermined frequency.

* * * * *